US011311202B2

(12) United States Patent
Bliss et al.

(10) Patent No.: US 11,311,202 B2
(45) Date of Patent: Apr. 26, 2022

(54) ROBUST REAL-TIME HEART RATE MONITORING METHOD BASED ON HEARTBEAT HARMONICS USING SMALL-SCALE RADAR

(71) Applicants: Daniel Bliss, Scottsdale, AZ (US); Yu Rong, Tempe, AZ (US)

(72) Inventors: Daniel Bliss, Scottsdale, AZ (US); Yu Rong, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 411 days.

(21) Appl. No.: 16/190,687

(22) Filed: Nov. 14, 2018

(65) Prior Publication Data

US 2019/0142289 A1    May 16, 2019

Related U.S. Application Data (60) Provisional application No. 62/586,125, filed on Nov. 14, 2017.

(51) Int. Cl.
*A61B 5/00* (2006.01)
*A61B 5/024* (2006.01)
(Continued)

(52) U.S. Cl.
CPC ........ *A61B 5/02444* (2013.01); *A61B 5/0507* (2013.01); *G01S 7/295* (2013.01);
(Continued)

(58) Field of Classification Search
CPC . A61B 5/02444; A61B 5/0507; G01S 17/295; G01S 7/352; G01S 13/52;
(Continued)

(56) References Cited

U.S. PATENT DOCUMENTS 9,737,219 B2    8/2017 Chen
9,971,027 B1*   5/2018 Stockmann ......... G01S 13/5244
(Continued)

FOREIGN PATENT DOCUMENTS

EP    3440991 A1    2/2019
EP    3440996 A1    2/2019
(Continued)

OTHER PUBLICATIONS

Li, Changzhi, et al., "Complex Signal Demodulation and Random Body Movement Cancellation Techniques for Non-contact Vital Sign Detection," Microwave Symposium Digest, 2008, IEEE, pp. 567-570.
(Continued)

*Primary Examiner* — Keith M Raymond
*Assistant Examiner* — Adam D. Kolkin
(74) *Attorney, Agent, or Firm* — Withrow & Terranova, P.L.L.C.

(57) ABSTRACT

The present disclosure relates to a heart rate monitoring method based on heartbeat harmonics. First, mixed data of a subject, which includes a fundamental respiration signal, respiration harmonics, a fundamental heartbeat signal, and heartbeat harmonics, is acquired by scanning a set of range bins. Range Doppler processing of the mixed data is performed to determine a range bin of interest. Data spectrum is then extracted based on a portion of the mixed data acquired at the range bin of interest. Next, the data spectrum is adaptively filtered to at least remove a spectrum peak of the fundamental respiration signal and a spectrum peak of the fundamental heartbeat signal mixed with a portion of respiration harmonics that are spectrally close to the fundamental heartbeat signal. Finally, the fundamental heartbeat signal is recovered based on a strongest heartbeat harmonic in the filtered data spectrum.

16 Claims, 9 Drawing Sheets

(51) Int. Cl.
  A61B 5/0507 (2021.01)
  G01S 7/295 (2006.01)
  G01S 7/35 (2006.01)
  G01S 13/58 (2006.01)
  G01S 13/52 (2006.01)
  G01S 13/02 (2006.01)

(52) U.S. Cl.
  CPC .............. *G01S 7/352* (2013.01); *G01S 13/52* (2013.01); *G01S 13/582* (2013.01); *G01S 13/584* (2013.01); *G01S 7/356* (2021.05); *G01S 13/0209* (2013.01)

(58) Field of Classification Search
  CPC .. G01S 13/582; G01S 13/584; G01S 13/0209; G01S 2007/356
  See application file for complete search history.

(56) References Cited

U.S. PATENT DOCUMENTS

| | | |
|---|---|---|
| 2008/0214903 A1 | 9/2008 | Orbach |
| 2013/0317377 A1 | 11/2013 | Gupta et al. |
| 2014/0276089 A1 | 9/2014 | Kirenko et al. |
| 2014/0276099 A1 | 9/2014 | Kirenko et al. |
| 2014/0276104 A1 | 9/2014 | Tao et al. |
| 2015/0379370 A1 | 12/2015 | Clifton et al. |
| 2016/0338604 A1 | 11/2016 | Wang et al. |
| 2016/0343135 A1 | 11/2016 | De Haan et al. |
| 2017/0042432 A1* | 2/2017 | Adib ................ G01S 7/415 |
| 2017/0127988 A1 | 5/2017 | Tao et al. |
| 2017/0174343 A1 | 6/2017 | Erickson et al. |
| 2018/0085009 A1 | 3/2018 | Aiello et al. |
| 2018/0140255 A1 | 5/2018 | Tao et al. |
| 2019/0050985 A1 | 2/2019 | Den Brinker et al. |
| 2019/0057502 A1 | 2/2019 | Wang et al. |

FOREIGN PATENT DOCUMENTS

| | | | |
|---|---|---|---|
| WO | 2013027027 A2 | 2/2013 | |
| WO | 2016185004 A1 | 11/2016 | |
| WO | WO-2017195196 A1 * | 11/2017 | ........... A61B 5/0205 |
| WO | 2019126476 A1 | 6/2019 | |
| WO | 2020072297 A1 | 4/2020 | |
| WO | 2020191142 A1 | 9/2020 | |

OTHER PUBLICATIONS

Rong, Yu, et al., "Harmonics-Based Multiple Heartbear Detection at Equal Distance using UWB Impulse Radar," IEEE Radar Conference, Apr. 2018, IEEE, pp. 1101-1105.
Zade, G. et al., "A Modern Microwave Life Detection System for Human Being Buried Under Rubble", International Journal of Advanced Engineering Research and Studies, Oct. 2011, vol. 1, 9 pages.
Fathy, Ramzie, et al., "Comparison of UWB Doppler radar and Camera based Photoplethysmography in Non-contact Multiple Heartbeats Detection," BioWireleSS, 2016, IEEE, pp. 25-28.
Feng, Litong, et al., "Motion-Resistant Remote Imaging Photoplethysmography Based on the Optical Properties of Skin," IEEE Transactions on Circuits and Systems for Video Technology, vol. 25, Issue 5, May 2015, pp. 879-891.
Gauri, Zade, "A Modem Microwave Life Detection System for Human Being Buried Under Rubble," International Journal of Advanced Engineering Research and Studies, vol. 1, Issue 1, Oct. 2011, 9 pages.
Hussain, Malek, "Ultra-Wideband Impulse Radar—An Overview of the Principles," IEEE AES Systems Magazine, vol. 13, Issue 9, Sep. 1998, pp. 9-14.
Lazaro, A., et al., "Analysis of Vital Signs Monitoring Using an IR-UWB Radar," Progress In Electromagnetics Research, vol. 100, 2010, pp. 265-284.
Park, Byung-Kown, et al., "Arctangent Demodulation With DC Offset Compensation in Quadrature Doppler Radar Receiver Systems," IEEE Transactions on Microwave Theory and Techniques, vol. 55, Issue 5, May 2007, pp. 1073-1079.
Poe, Ming-Zher, et al., "Non-contact, automated cardiac pulse measurements using video imaging and blind source separation," Optics Express, vol. 18, Issue 10, May 2010, 13 pages.
Singh, Megha, et al., "Reconstruction of Sequential Cardiac In-Plane Displacement Patterns on the Chest Wall by Laser Speckle Interferometry," IEEE Transactions on Biomedical Engineering, vol. 38, Issue 5, May 1991, pp. 483-489.
Wang, Jingyu, et al., "Noncontact Distance and Amplitude-Independent Vibration Measurement Based on an Extended DACM Algorithm," IEEE Transactions on Instrumentation and Measurement, vol. 63, Issue 1, Jan. 2014, pp. 145-153.
Yan, Jiaming, et al., "Through-Wall Multiple Targets Vital Signs Tracking Based on VMD Algorithm," Sensors, vol. 16, Issue 8, Aug. 2016, 11 page.
Ren, Lingyun, et al., "Noncontact Heartbeat Detection using UWB Impulse Doppler Radar," BioWireleSS, 2015, IEEE, pp. 14-16.
Al-Naji, A. et al., "Remote Optical Cardiopulmonary Signal Extraction With Noise Artifact Removal, Multiple Subject Detection & Long-Distance," IEEE Access, vol. 6, 2018, IEEE, pp. 11573-11595.
Author Uknown, "Apple Watch Series 5," accessed Nov. 16, 2018 from https://www.apple.com/apple-watch-series-4/health/, 13 pages.
Author Uknown, "Shimmer3 ECG Unit," accessed Nov. 16, 2018 from http://www.shimmersensing.com/products/shimmer3-ecg sensor, 6 pages.
Doerry, A., "Just Where Exactly is the Radar? (a.k.a. The Radar Antenna Phase Center)," Sandia Report SAND2013-10635, Dec. 2013, Sandia National Laboratories, 26 pages.
Fox, K. et al., "Resting Heart Rate in Cardiovascular Disease," Journal of the American College of Cardiology, vol. 50, No. 9, 2007, Elsevier Inc., pp. 823-830.
Guan, S. et al., "Automated DC Offset Calibration Strategy for Structural Health Monitoring Based on Portable CW Radar Sensor," IEEE Transactions on Instrumentation and Measurement, vol. 63, No. 12, Dec. 2014, IEEE, pp. 3111-3118.
Li, Changzhi, "Doppler Phase Modulation Effect for Non-contact Accurate Measurement of Vital Signs and other Periodic Movements—From Theory to CMOS System on Chip Integrations," A Dissertation presented to the Graduate School of the University of Florida, 2009, 129 pages.
Lin, J., "Noninvasive Microwave Measurement of Respiration," Proceedings of the IEEE, Oct. 1975, IEEE, p. 1530.
Ren, L. et al., "Phase-Based Methods for Heart Rate Detection Using UWB Impulse Doppler Radar," IEEE Transactions on Microwave Theory and Techniques, vol. 64, Issue 10, Oct. 2016, IEEE, 13 pages.
Rong, Y. et al., "Direct RF Signal Processing For Heart-Rate Monitoring Using UWB Impulse Radar," 2018 52nd Asilomar Conference on Signals, Systems, and Computers, Oct. 28-31, 2018, Pacific Grove, CA, IEEE, pp. 1215-1219.
Rong, Y. et al., "Remote Sensing for Vital Information Based on Spectral-Domain Harmonic Signatures," IEEE Transactions on Aerospace and Electronic Systems, vol. 55, No. 6, Dec. 2019, OAPA, pp. 3454-3465.
Singh, A. et al., "Data-Based Quadrature Imbalance Compensation for a CW Doppler Radar System," IEEE Transactions on Microwave Theory and Techniques, vol. 61, No. 4, Apr. 2013, IEEE, pp. 1718-1724.
Wang, S. et al., "A Novel Ultra-Wideband 80 GHz FMCW Radar System for Contactless Monitoring of Vital Signs," 2015 37th Annual International Conference of the IEEE Engineering in Medicine and Biology Society (EMBC), Aug. 25-29, 2015, Milan, Italy, IEEE, pp. 4978-4981.
Wolff, C., "Organ-Pipe Scanner," accessed Feb. 2019 from https://www.radartutorial.eu/06.antennas/an66.en.html, 1 page.
International Search Report and Written Opinion for International Patent Application No. PCT/US2020/023533, dated Jun. 18, 2020, 11 pages.

(56) References Cited

OTHER PUBLICATIONS

Nowara, E. et al., "PPGSecure: Biometric Presentation Attack Detection Using Photopletysmograms," 12th IEEE International Conference on Automatic Face & Gesture Recognition (FG 2017), May 30-Jun. 3, 2017, Washington, DC, USA, IEEE, 3 pages.
O'Brien, S., "Deepfakes are coming. Is Big Tech ready?" CNN Money, Aug. 8, 2018, 3 pages.
Wiede, C. et al., "Remote Heart Rate Determination in RGB Data," Proceedings of the 5th International Conference on Pattern Recognition Applications and Methods (ICPRAM 2016), Feb. 2016, Scitepress, pp. 240-246.
Youseph, S. et al., "Pixel and Edge Based Illuminant Color Estimation for Image Forgery Detection," Procedia Computer Science, vol. 46, Oct. 2015, Elsevier B.V., 8 pages.
Non-Final Office Action for U.S. Appl. No. 16/823,587, dated Nov. 23, 2021, 19 pages.

\* cited by examiner

ROBUST REAL-TIME HEART RATE MONITORING METHOD BASED ON HEARTBEAT HARMONICS USING SMALL-SCALE RADAR

RELATED APPLICATIONS

This application claims the benefit of provisional patent application Ser. No. 62/586,125, filed Nov. 14, 2017, the disclosure of which is hereby incorporated herein by reference in its entirety.

FIELD OF THE DISCLOSURE

The present disclosure relates to a real-time heart rate monitoring method based on heartbeat harmonics using small-scale radar.

BACKGROUND

Vital sign information extraction, especially heart rate (heartbeat waveform), has important implications for human health. Conventionally, Electrocardiography (ECG or EKG) devices and finger pulse oximeters have been widely used up to now, because they may provide medical standard results for medical professionals. However, these methods require direct contract with a human body, which may generate discomfort and may not be suitable for prolonged monitoring, and thereby cannot be applied for certain patients.

Alternatively, camera based photoplethysmography systems have been proposed for heart rate detection and the results are very promising. This is an optical method to measure the change of blood volume. However, this camera based approach requires sufficient lighting for the exposed skin, which may not always be practical.

Accordingly, there remains a need for an improved heart rate monitoring method that provides a remote monitoring technique without direct contract with the human body and without strict lighting requirements. In addition, there is also a need to implement a low-cost monitoring method and robust related signal processing techniques.

SUMMARY

The present disclosure relates to a real-time heart rate monitoring method based on heartbeat harmonics using small-scale radar. According to an exemplary process, a set of range bins is scanned by small-scale radar to acquire mixed data of a subject. Herein, the mixed data includes respiration data and heartbeat data. The respiration data includes a fundamental respiration signal and respiration harmonics, and the heartbeat data includes a fundamental heartbeat signal and heartbeat harmonics. Next, range Doppler processing of the mixed data is performed by a computer to determine a range bin of interest in the range bins, where a portion of the mixed data acquired at the range bin of interest contains a highest energy level of the mixed data. Data spectrum of the mixed data is then extracted based on at least the portion of the mixed data acquired at the range bin of interest. Adaptive filtering is applied to the data spectrum by the computer to at least remove a spectrum peak of the fundamental respiration signal and a spectrum peak of the fundamental heartbeat signal mixed with a portion of respiration harmonics that are spectrally close to the fundamental heartbeat signal. Lastly, the fundamental heartbeat signal is recovered based on a strongest heartbeat harmonic in the filtered data spectrum.

In one embodiment of the exemplary process, the range bins are scanned repeatedly by the small-scale radar to acquire multiple sets of the mixed data. The multiple sets of mixed data are correspondingly summed together. A phase noise correction is then applied to the mixed data to reduce the phase noise due to sampling jitter before performing the range Doppler processing.

In one embodiment of the exemplary process, the small-scale radar is one of a group consisting of Ultra-Wideband (UWB) radar, frequency-modulated continuous wave (FMCW) radar, and impulse based radar.

In one embodiment of the exemplary process, a scope of the range bins is between 0.2 meter and 3 meters. Herein, the subject is located within the scope of the range bins.

According to another embodiment, the exemplary process further includes performing clutter suppression to remove static background before performing range Doppler processing of the mixed data. Herein, the clutter suppression is realized by high-pass filtering.

According to another embodiment, the exemplary process further includes coherently combining the portion of the mixed data acquired at the range bin of interest with other portions of the mixed data acquired at nearby range bins to provide combined data before extracting the data spectrum. Herein, the combined data has a greater SNR than the mixed data acquired at the range bin of interest.

In one embodiment of the exemplary process, a distance between the range bin of interest and each of the nearby range bins is less than 0.2 meter.

In one embodiment of the exemplary process, coherently combining the portion of the mixed data acquired at the range bin of interest with the other portions of the mixed data acquired at nearby range bins is implemented by summing the portion of the mixed data acquired at the range bin of interest and the other portions of the mixed data acquired at nearby range bins together, correspondingly.

In one embodiment of the exemplary process, extracting the data spectrum is based on the combined data.

According to another embodiment, the exemplary process further includes performing spectrum analysis to find the spectrum peak of the fundamental respiration signal, and determine a lower limit of the adaptive filtering based on the spectrum peak of the fundamental respiration signal. The lower limit ensures the removal of the spectrum peak of the fundamental respiration signal and the spectrum peak of the fundamental heartbeat signal mixed with the portion of respiration harmonics that are spectrally close to the fundamental heartbeat signal.

In one embodiment of the exemplary process, the adaptive filtering is implemented by a low-pass filter or a band-pass filter.

According to another embodiment, the exemplary process further includes performing high-pass filtering to reduce DC residues before performing spectrum analysis.

According to another embodiment, the exemplary process further includes determining a harmonic order of the strongest heartbeat harmonic in the filtered data spectrum before recovering the fundamental heartbeat signal. Herein, a frequency of the fundamental heartbeat signal is recovered by dividing a frequency of the strongest heartbeat harmonic with the harmonic order of the strongest heartbeat harmonic.

According to another exemplary process, mixed data of a first subject and a second subject at a set of range bins is acquired simultaneously by the small-scale radar. Herein, the mixed data includes first respiration data and first heartbeat data of the first subject, and second respiration data and second heartbeat data of the second subject. The first respiration data includes a first fundamental respiration signal and first respiration harmonics, and the first heartbeat data includes a first fundamental heartbeat signal and first heartbeat harmonics. The second respiration data includes a second fundamental respiration signal and second respiration harmonics, and the second heartbeat data includes a second fundamental heartbeat signal and second heartbeat harmonics. Next, range Doppler processing of the mixed data is performed by a computer to determine a first range bin of interest and a second range bin of interest in the range bins. A portion of the mixed data acquired at the first range bin of interest and a portion of the mixed data acquired at the second range bin of interest have the highest two energy levels of the mixed data. Data spectrum of the mixed data is extracted based on at least the portion of the mixed data acquired at the first range bin of interest and the portion of the mixed data acquired at the second range bin of interest. The data spectrum is adaptively filtered by the computer to at least remove a spectrum peak of the first fundamental respiration signal, a spectrum peak of the first fundamental heartbeat signal mixed with a portion of the first respiration harmonics that are spectrally close to the first fundamental heartbeat signal, a spectrum peak of the second fundamental respiration signal, a spectrum peak of the second fundamental heartbeat signal mixed with a portion of the second respiration harmonics that are spectrally close to the second fundamental heartbeat signal. At last, the first fundamental heartbeat signal and the second fundamental heartbeat signal are recovered based on two strongest heartbeat harmonics in the filtered data spectrum.

In one embodiment of the exemplary process, the first subject and the second subject are located at a same distance from the small-scale radar. Herein, the first subject and the second subject have heart rates with at least a difference of 5 BPM.

In one embodiment of the exemplary process, the first subject and the second subject are located at different distances from the small-scale radar.

In one embodiment of the exemplary process, the first subject and the second subject are located at different angles from the small-scale radar.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

It will be understood that for clear illustrations, FIGS. 1-9 may not be drawn to scale.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1:
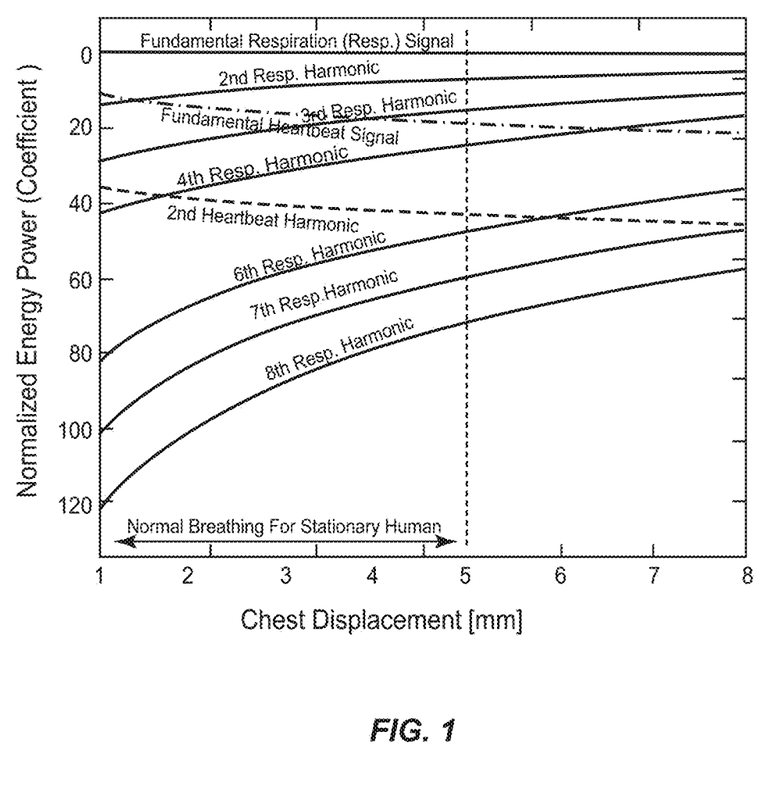
FIG. 1 shows normalized energy power of a fundamental respiration signal, respiration harmonics, a fundamental heartbeat signal, and heartbeat harmonics.

The present disclosure relates to a real-time heart rate monitoring method based on heartbeat harmonics using small-scale radar. It is well known to those skilled in the art that heartbeat signals are always coupled with chest movement (respiration signals). For normal breathing of a stationary human, when the chest displacement is between 1 mm and 5 mm, energy of a fundamental heartbeat signal (top dashed line) is about 12-20 dB down compared to energy of a fundamental respiration signal (top solid line), as illustrated in FIG. 1. Energy of a $2^{nd}$ order heartbeat harmonic (bottom dashed line) is about 20 dB down compared to the energy of the fundamental heartbeat signal, and is about 32-40 dB down compared to the energy of the fundamental respiration signal. In addition, energy of a $2^{nd}$ order respiration harmonic (second solid line, from top to bottom) is about 9-15 dB down compared to the energy of the fundamental respiration signal, energy of a $3^{rd}$ order respiration harmonic (third solid line, from top to bottom) is about 18-30 dB down compared to the energy of the fundamental respiration signal, and energy of a $4^{th}$ order respiration harmonic (fourth solid line, from top to bottom) is about 30-45 dB down compared to the energy of the fundamental respiration signal. Further, energy of higher order respiration harmonics (solid lines), such as $6^{th}$, $7^{th}$, or $8^{th}$, may be more than 50 dB down compared to the energy of the fundamental respiration signal. It is clear that the fundamental respiration signal has the strongest energy. The fundamental heartbeat signal is weaker than the fundamental respiration signal, and comparable to the $2^{nd}$ and $3^{rd}$ order respiration harmonics. The $2^{nd}$ order heartbeat harmonic is weaker than the $2^{nd}$ and $3^{rd}$ order respiration harmonics, comparable to the $4^{th}$ order respiration harmonic, and stronger than the $6^{th}$, $7^{th}$, and $8^{th}$ order respiration harmonics.

Figure 2:
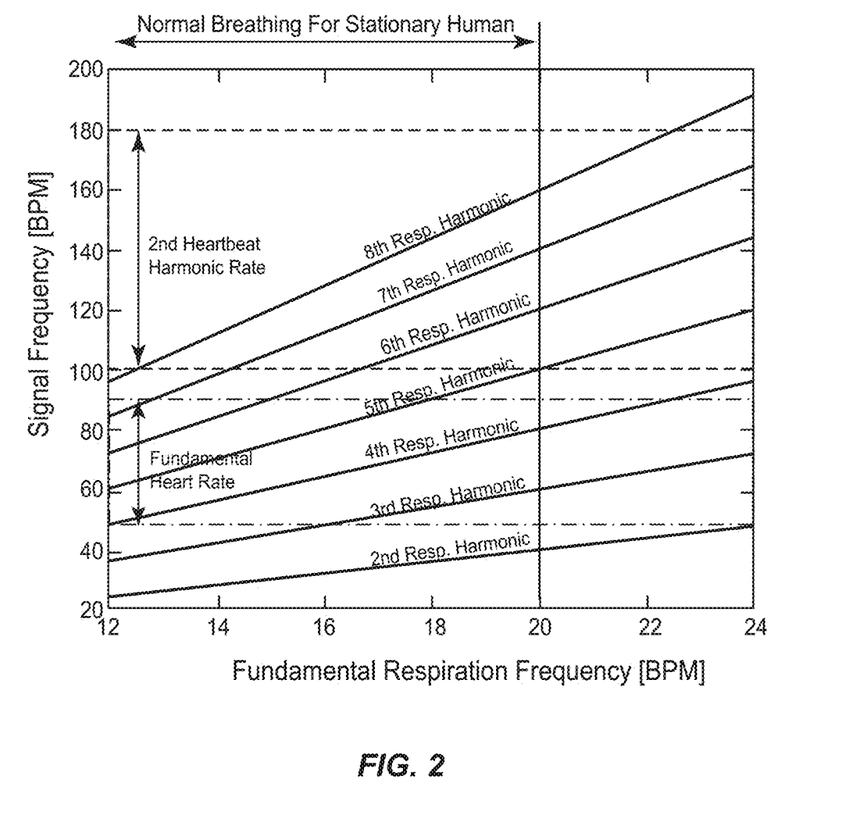
FIG. 2 shows signal frequency ranges of the fundamental respiration signal, the respiration harmonics, the fundamental heartbeat signal, and the heartbeat harmonics.

FIG. 2 shows signal frequency ranges of the fundamental respiration signal, the respiration harmonics, the fundamental heartbeat signal, and the heartbeat harmonics. For normal breathing of a stationary human, the fundamental respiration signal has a frequency range between 12 and 20 breaths/beats per minute (BPM). As such, the $2^{nd}$, $3^{rd}$, $4^{th}$, $5^{th}$, $6^{th}$, $7^{th}$, and $8^{th}$ order respiration harmonics have frequency ranges (solid lines) between 24 and 40 BPM, between 36 and 60 BPM, between 48 and 80 BPM, between 60 and 100 BPM, between 72 and 120 BPM, between 84 and 140 BPM, and between 96 and 160 BPM, respectively. The fundamental heartbeat signal has a frequency range (between bottom two dashed lines) between 50 and 90 BPM, and the $2^{nd}$ order heartbeat harmonic has a frequency range (between top two dashed lines) between 100 and 180 BPM. It is clear that the fundamental heartbeat signal may have frequency overlaps with the $3^{rd}$, $4^{th}$, $5^{th}$, and/or $6^{th}$ order respiration harmonics, while the $2^{nd}$ order heartbeat harmonic may have frequency overlaps with $6^{th}$, $7^{th}$, and/or $8^{th}$ order respiration harmonics.

Herein, the fundamental heartbeat signal may have frequency overlaps with the $3^{rd}$, $4^{th}$, $5^{th}$, and/or $6^{th}$ order respiration harmonics, and may have energy comparable to the $2^{nd}$ and $3^{rd}$ order respiration harmonics, such that it is difficult to separate the fundamental heartbeat signal from the respiration harmonics (ex, the $3^{rd}$ order respiration harmonic). On the other hand, although the $2^{nd}$ order heartbeat harmonic may have frequency overlaps with $6^{th}$, $7^{th}$, and/or $8^{th}$ order respiration harmonics, the $2^{nd}$ order heartbeat harmonic has a stronger energy than the $6^{th}$, $7^{th}$, and $8^{th}$ order respiration harmonics. Therefore, a clean spectrum of the $2^{nd}$ order heartbeat harmonic with negligible respiration harmonics may be obtained. Similarly, a $3^{rd}$ order heartbeat harmonic (not shown) may also be separate from the respiration harmonics (the $3^{rd}$ order heartbeat harmonic may have frequency overlaps with the $8^{th}$ and higher order respiration harmonics, however, the $3^{rd}$ order heartbeat harmonic is only 52-60 dB down compared to the energy of the fundamental respiration signal, which is much stronger than the $8^{th}$ and higher order respiration harmonics). Therefore, the $2^{nd}$ order heartbeat harmonic or the $3^{rd}$ order heartbeat harmonic may be utilized to recover the fundamental heartbeat signal instead of extracting the fundamental heartbeat signal directly.

Figure 3:
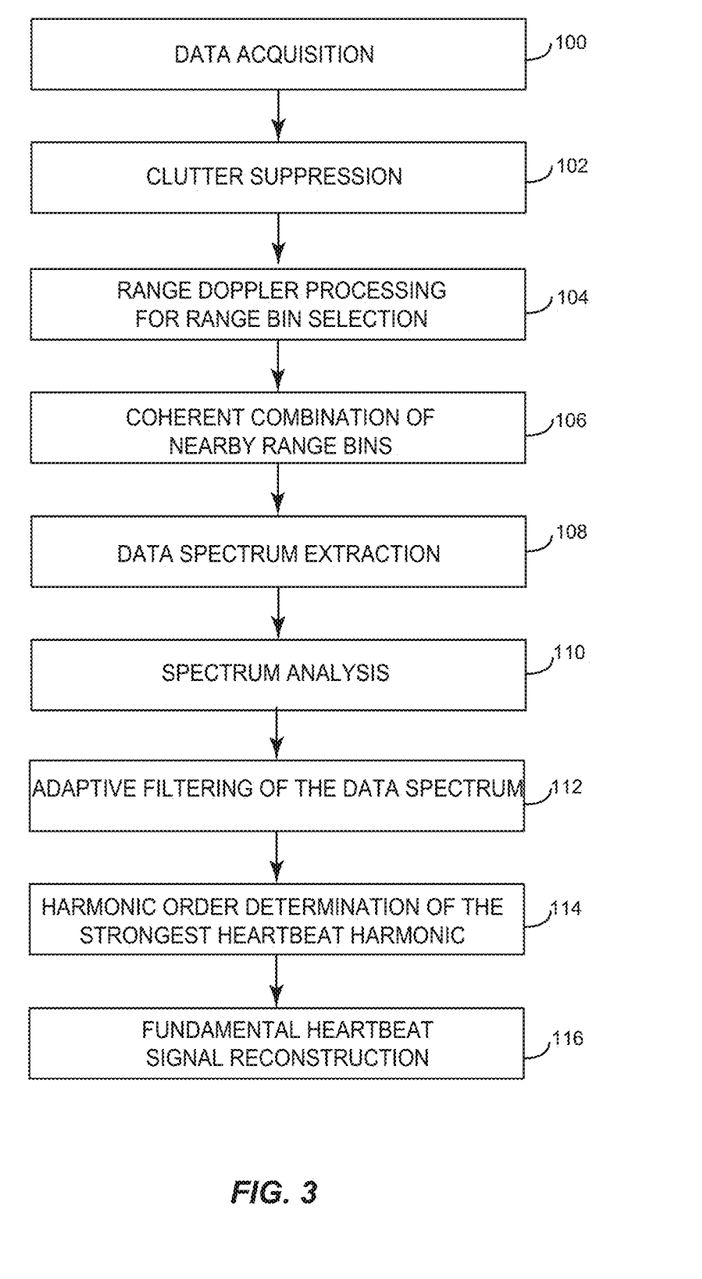
FIG. 3 shows a flow diagram that illustrates an exemplary process to monitor a heart rate according to one embodiment of the present disclosure.

FIG. 3 shows a flow diagram that illustrates exemplary steps to monitor heart rate of a stationary human according to one embodiment of the present disclosure. Although the exemplary steps are illustrated in a series, the exemplary steps are not necessarily order dependent. Some steps may be done in a different order than that presented. Further, processes within the scope of this disclosure may include fewer or more steps than those illustrated in FIG. 3.

Initially, a small-scale radar is used to scan a set of range bins to acquire mixed data of a subject, for instance, a stationary human (step 100). A scope of the scanned range bins must be within the detection range of the small-scale radar, such as between 0.2 meter and 2 meters, or between 0.5 meter and 3 meters. The subject is located within the scope of the scanned range bins. Herein, the mixed data includes respiration data and heartbeat data. The respiration data includes a fundamental respiration signal and respiration harmonics, and the heartbeat data includes a fundamental heartbeat signal and heartbeat harmonics. The small-scale radar may be a centimeter or millimeter wavelength radar, with a detection range of a couple of meters, such as Ultra-Wideband (UWB) radar, frequency-modulated continuous wave (FMCW) radar, or impulse based radar. In order to increase a signal to noise ratio (SNR), the range bins are repeatedly scanned by the small-scale radar to acquire multiple sets of the mixed data. These multiple sets of mixed data are correspondingly summed together. A phase noise correction is then applied to the summed mixed data to reduce the phase noise due to sampling jitter. The phase noise correction may be implemented by applying a phase shift to the mixed data at each range bin with respect to a mean phase in a reference range bin (ex, using the first range bin, which is related to a direct path from transmit antenna to receiver antenna, as the reference range bin) in the baseband. The phase information from the reference range bin should be constant over time.

Figure 4:
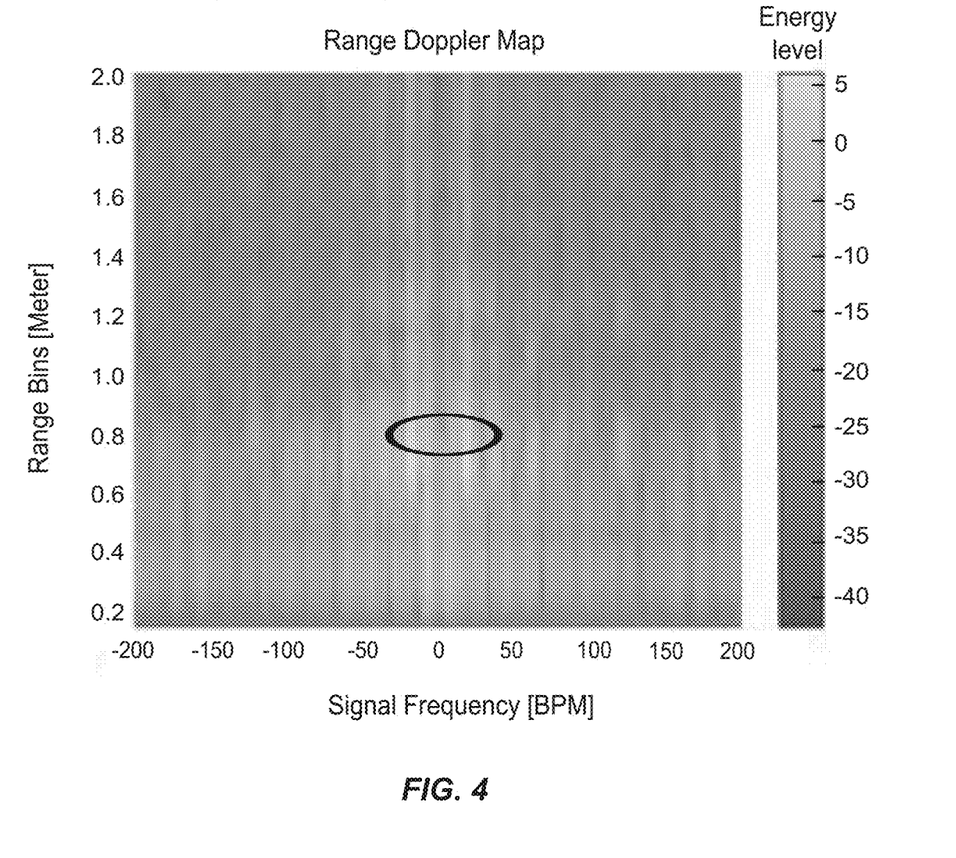
FIG. 4 shows a range Doppler map.

Next, clutter suppression is performed on the acquired mixed data to remove static background (step 102). The clutter suppression may be realized by high-pass filtering. In some applications, the clutter suppression may be omitted. A range Doppler processing of the mixed data is followed to determine a range bin of interest for the subject (step 104). Herein, the range bin of interest refers to a range bin at which a portion of the mixed data acquired for the subject contains the highest energy within the mixed data. FIG. 4 shows a range Doppler map of the mixed data obtained by the range Doppler processing. In this example, a portion of the mixed data at a range bin of 0.8 meter has the highest energy level. As such, the range bin of interest for the subject is 0.8 meter. Typically, the range bin of interest indicates a distance between the subject and the small-scale radar. If the mixed data is clutter suppressed, the clutter suppression may be performed before the range Doppler processing of the mixed data.

In reality, the energy of the mixed data will not be concentrated at the range bin of interest. Instead, the energy of the mixed data is spread across multiple range bins near the range bin of interest. In one embodiment, the portion of the mixed data acquired at the range bin of interest may be coherently combined with other portions of the mixed data acquired at the nearby range bins to provide combined data (step 106). Herein, a distance between the range bin of interest and each of the nearby range bins may be less than 0.2 meter, or less than 0.1 meter. For instance, if the range bin of interest is at 1 meter away from the small-scale radar, the nearby range bins considered are between 0.9 meter and 1.1 meters away from the small-scale radar, or between 0.8 meter and 1.2 meters away from the small-scale radar. The combined data may have a greater SNR than the mixed data acquired at the range bin of interest. To further optimize the SNR of the combined data, the portion of the mixed data acquired at the range bin of interest and the portion of the mixed data acquired at each nearby range bin may be combined with different weights. The weights may be determined by singular value decomposition of a covariance matrix formed from the mixed data.

Data spectrum of the fundamental respiration signal, the respiration harmonics, the fundamental heartbeat signal, and the heartbeat harmonics is then extracted based on the combined data (step 108). In some applications, there may be no coherent combination step, and the data spectrum will be extracted based on the portion of the mixed data acquired at the range bin of interest. The data spectrum may be extracted by applying Fast Fourier Transform (FFT) to the combined data (or to the portion of the mixed data acquired at the range bin of interest if there is no coherent combination step).

Figure 5:
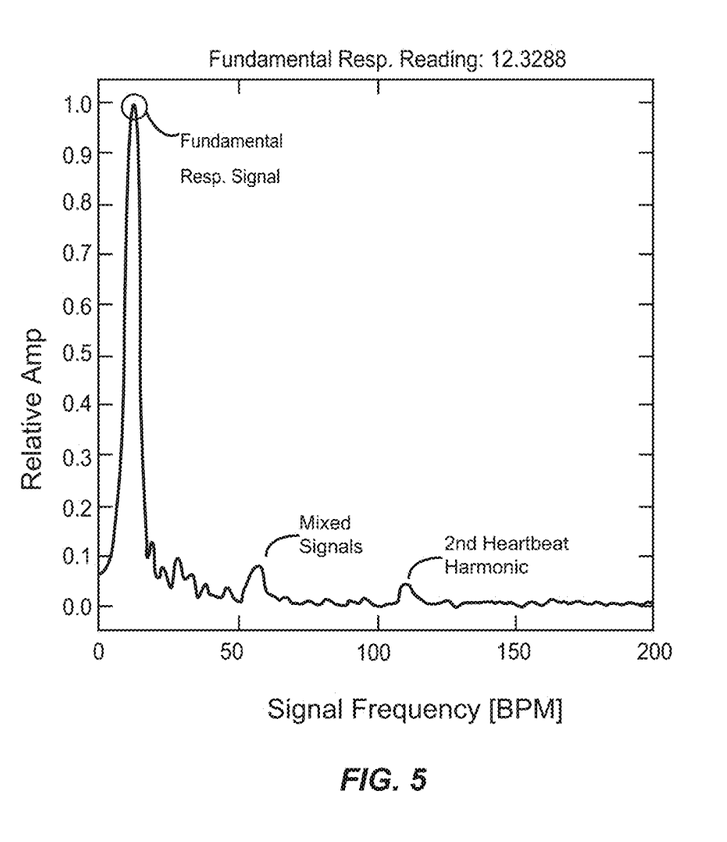
FIG. 5 shows data spectrum.

After the data spectrum is obtained, as illustrated in FIG. 5, spectrum analysis is performed to find a spectrum peak of the fundamental respiration signal (step 110). A high-pass filter may be applied to the data spectrum (not shown) to reduce DC residues before performing the spectrum analysis. Since the respiration harmonics, the fundamental heartbeat signal, and the heartbeat harmonics have a much weaker energy than the fundamental respiration signal, the maximum spectrum peak within the data spectrum must be from the fundamental respiration signal. In this example, the spectrum peak of the fundamental respiration signal is 12.3288 BMP. As such, the second order respiration harmonic is 24.6576 BMP, the third order respiration harmonic is 36.9864 BMP, the fourth order respiration harmonic is 49.3152 BMP, and the fifth order respiration harmonic is 61.644 BMP. For normal breathing of a stationary human, the fundamental heartbeat signal has a frequency range between 50 and 90 BPM, such that a spectrum peak around 55 BPM may come from a combination of the fundamental heartbeat signal, the third order respiration harmonic, the fourth order respiration harmonic, and the fifth order respiration harmonic. As such, it is difficult to separate the fundamental heartbeat signal from the respiration harmonics.

In FIG. 5, there is another spectrum peak at around 110 BMP. Since the spectrum peak of the fundamental respiration signal is 12.3288 BMP, at least the $8^{th}$ or higher order respiration harmonics may have a frequency around or over 100 BMP. Fortunately, the $8^{th}$ and higher order respiration harmonics have negligible energy; therefore, the spectrum peak at around 110 BMP must be the $2^{nd}$ heartbeat harmonic or the $3^{rd}$ heartbeat harmonic.

Figure 6:
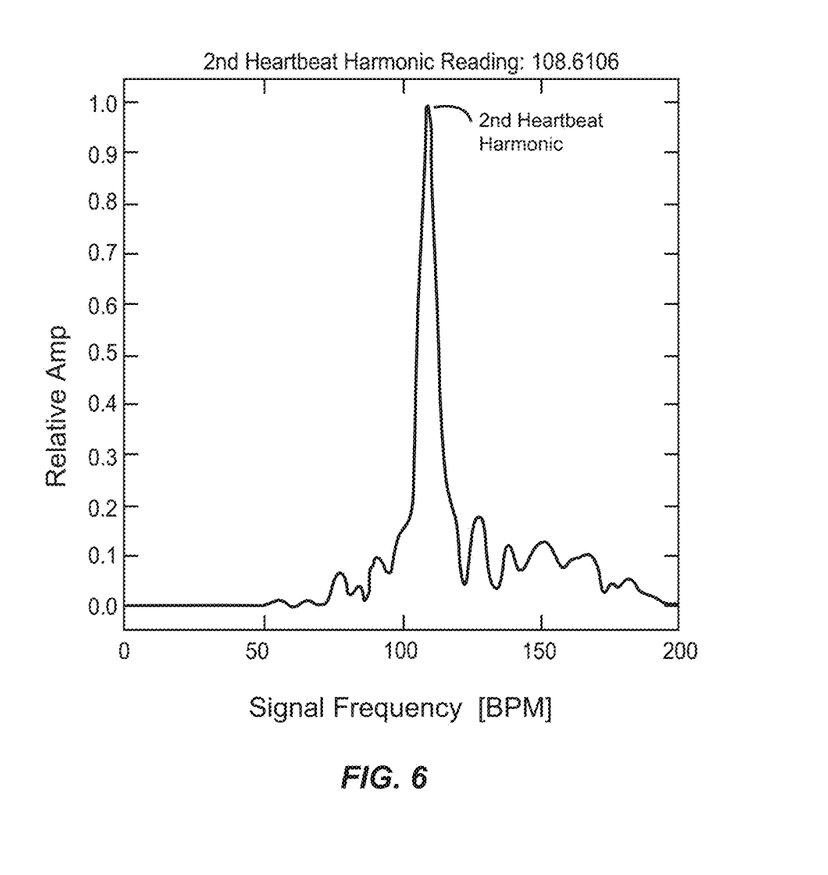
FIG. 6 shows filtered data spectrum.

Next, an adaptive filter is applied to the data spectrum (step 112). Herein, the adaptive filter has a lower limit to ensure the removal of the spectrum peak of the fundamental respiration signal, the spectrum peak of the mixed signals (here are the second order respiration harmonic, the third order respiration harmonic, the fifth order respiration harmonic, and the fundamental heartbeat signal). FIG. 6 shows a filtered data spectrum with a spectrum peak at 108.6106 BMP. In this example, the spectrum peak at 108.6106 BMP is the strongest spectrum peak in the filtered data spectrum. In different applications, the adaptive filter may have different lower limits to ensure the removal of the spectrum peak of the fundamental respiration signal, and the spectrum peak of the mixed signals that include the fundamental heartbeat signal and spectrally close respiration harmonics. Typically, the lower limit is multiple times the frequency of the fundamental respiration signal. The adaptive filter may be a low-pass filter or a band-pass filter.

Herein, the harmonic order of the strongest heartbeat peak in the filtered data spectrum needs to be determined before recovering the fundamental heartbeat signal (step 114). If the spectrum peak at 108.6106 BMP is the $2^{nd}$ order heartbeat harmonic, there should be a spectrum peak at 55 BMP for the fundamental heartbeat signal and the spectrum peak at 55 BMP must be stronger than the spectrum peak at 108.6106 BMP. If the spectrum peak at 108.6106 BMP is the $3^{rd}$ order heartbeat harmonic, there should be a spectrum peak at 36 BMP for the fundamental heartbeat signal and a spectrum peak at 72 BMP for the $2^{nd}$ order heartbeat harmonic. The spectrum peaks at 36 BMP and 72 BMP must be stronger than the spectrum peak at 108.6106 BMP. In this example, there is a spectrum peak at around 55 BMP stronger than the spectrum peak at 108.6106 BMP, but there is no spectrum peak at around 36 BMP or 72 BMP stronger than the spectrum peak at 108.6106 BMP. Therefore, the spectrum peak at 108.6106 BMP is the $2^{nd}$ order heartbeat harmonic.

Figure 7:
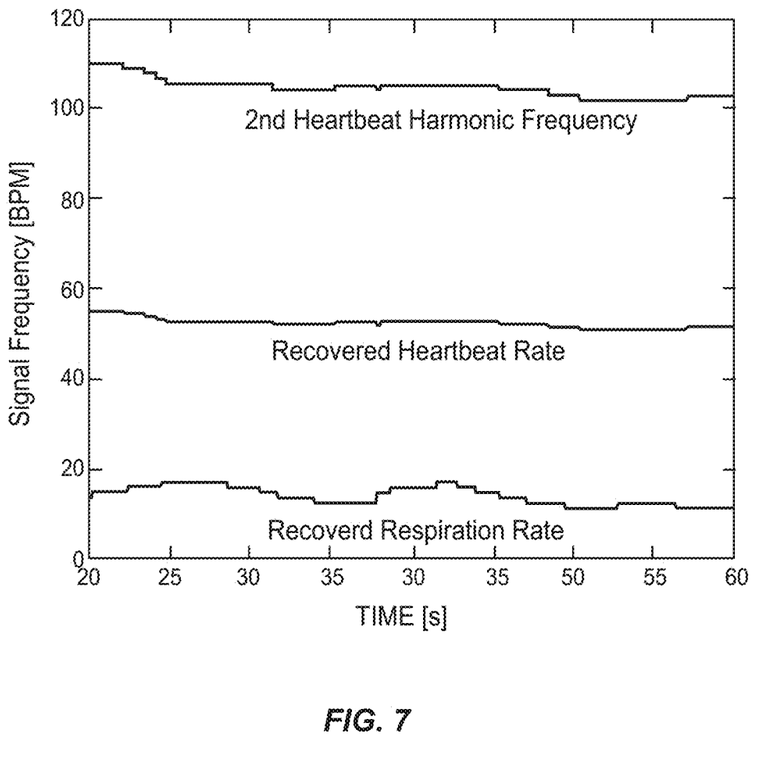
FIG. 7 shows signal frequencies of recovered signals.
Figure 8:
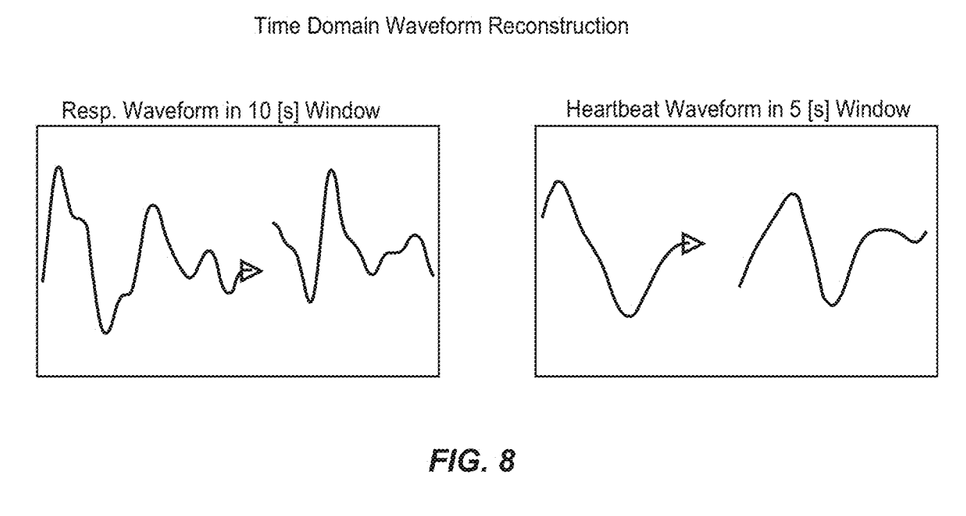
FIG. 8 shows time-domain waveform reconstructions.

Lastly, the fundamental heartbeat signal is recovered based on the strongest heartbeat harmonic in the filtered data spectrum (step 116). The heart rate (frequency of the fundamental heartbeat signal) is recovered by dividing the frequency of the strongest heartbeat harmonic (herein, the $2^{nd}$ order heartbeat harmonic) with the harmonic order (herein, 2). Herein, the frequency of the fundamental heartbeat signal is 54.3053 BMP. FIG. 7 shows the signal frequencies of the $2^{nd}$ order heartbeat harmonic, the recovered heart rate, and the recovered respiration rate. FIG. 8 shows time-domain waveform reconstructions of the fundamental respiration signal and the fundamental heartbeat signal. Notice that once the heart rate is known, the time-domain waveform reconstruction of the fundamental heartbeat signal may be obtained by applying one or more narrow spectral filters around the frequency of the fundamental heartbeat signal.

In some applications, multiple heart rates may be monitored at a same time. Similar to monitoring a single heart rate, monitoring two heart rates starts with data acquisition. Initially, mixed data of a first subject and a second subject at a set of range bins are simultaneously acquired by a small-scale radar. Herein, the mixed data includes first respiration data and first heartbeat data of the first subject, and second respiration data and second heartbeat data of the second subject. The first respiration data includes a first fundamental respiration signal and first respiration harmonics, and the first heartbeat data includes a first fundamental heartbeat signal and first heartbeat harmonics. The second respiration data includes a second fundamental respiration signal and second respiration harmonics, and the second heartbeat data includes a second fundamental heartbeat signal and second heartbeat harmonics.

Next, a range Doppler processing of the mixed data is performed to determine a first range bin of interest and a second range bin of interest in the set of range bins, which indicates distances between the first subject and the small-scale radar, and between the second subject and the small-scale radar, respectively. Herein, a portion of the mixed data acquired at the first range bin of interest and a portion of the mixed data acquired at the second range bin of interest have the highest two energy levels within the mixed data. In some applications, clutter suppression may be performed before the range Doppler processing to remove static background.

Data spectrum of the mixed data is then extracted based on the portion of the mixed data acquired at the first range bin of interest and the portion of the mixed data acquired at the second range bin of interest. In order to improve the SNR, the portion of the mixed data acquired at the first range bin of interest may be coherently combined with one portion of the mixed data acquired at first nearby range bins (close to the first range bin of interest) before the data spectrum extraction. In addition, the portion of the mixed data acquired at the second range bin of interest may be coherently combined with other portions of the mixed data acquired at second nearby range bins (close to the second range bin of interest) before the data spectrum extraction.

Adaptive filtering is followed to filter the data spectrum to at least remove spectrum peaks of the first fundamental respiration signal, the second fundamental respiration signal, the first fundamental heartbeat signal, first respiration harmonics spectrally close to the first fundamental heartbeat signal, the second fundamental heartbeat signal, and second respiration harmonics spectrally close to the second fundamental heartbeat signal. Lastly, the first fundamental heartbeat signal and the second fundamental heartbeat signal are recovered based on a strongest first heartbeat harmonic and a strongest second heartbeat harmonic in the filtered data spectrum.

Figure 9:
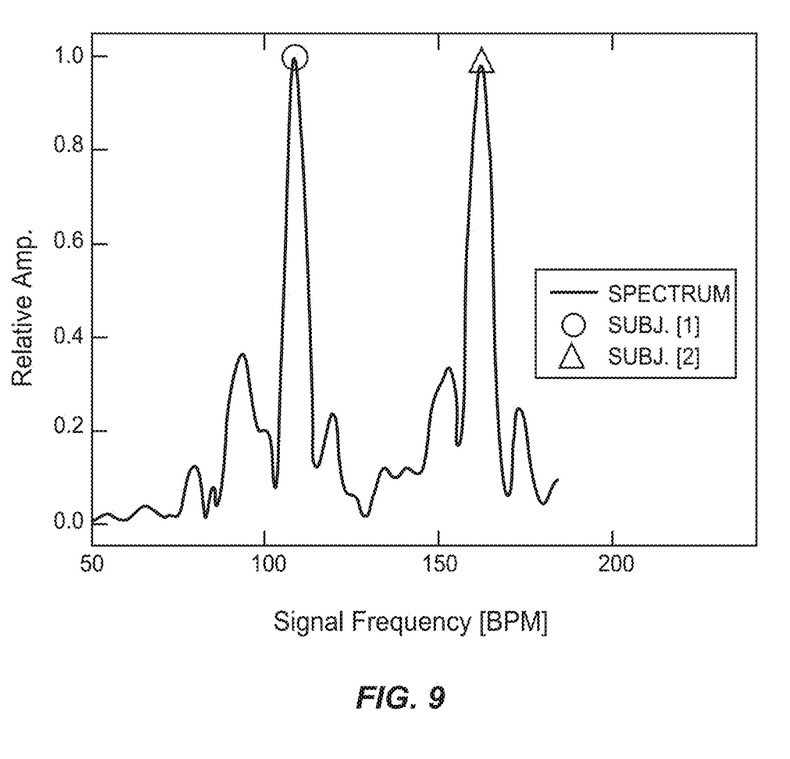
FIG. 9 shows filtered data spectrum for two subjects.

In one embodiment, the first subject and the second subject are located at a same distance from the small-scale radar, such that the first range bin of interest is the same as the second range bin of interest. If the first subject and the second subject have heart rates with at least a difference of 5 BPM, the first fundamental heartbeat signal and the second fundamental heartbeat signal may be separate from each other, and consequently may be recovered at the same time. FIG. 9 shows a filtered data spectrum for both the first subject and the second subject located at the same distance from the small-scale radar. A first spectrum peak of a $2^{nd}$ order heartbeat harmonic for the first subject is at 110 BPM, and a second spectrum peak of a $2^{nd}$ order heartbeat harmonic for the second subject is at 162 BPM. As such, the first heartbeat rate for the first subject is 55 BMP, which is distinguished from the second heartbeat rate for the second subject at 81 BMP. In another embodiment, range separation and/or angular separation between the first subject and the second subject may be utilized to detect and recover the first heartbeat rate for the first subject and a second heartbeat rate for the second subject.

Those skilled in the art will recognize improvements and modifications to the preferred embodiments of the present disclosure. All such improvements and modifications are considered within the scope of the concepts disclosed herein and the claims that follow.

What is claimed is:

1. A method comprising:
   acquiring mixed data of a subject by scanning a plurality of range bins by small-scale radar based on a signal model, wherein:
   the mixed data includes respiration data and heartbeat data;
   the respiration data includes a fundamental respiration signal and respiration harmonics;
   the heartbeat data includes a fundamental heartbeat signal and heartbeat harmonics; and
   the signal model is $y(t, \tau) = A_T p(\tau - \tau_D(t)) e^{-j2\pi v_c \tau}$, wherein:
   $y(t, \tau)$ denotes the mixed data;
   $A_T$ is an amplitude of a target response of a vital activity of the subject;
   where $p(t, \tau)$ is a generated short pulse, centered at a carrier frequency $v_c$;
   $\tau_D(t) = 2d(t)/c$ wherein c is a frequency of light;
   $d(t) = d_0 + m_b \sin(2\pi f_b t) + m_h \sin(2\pi f_h t)$, wherein $d(t)$ denotes vital activities of the subject located at a nominal distance $d_0$, $m_b$ is an amplitude of a respiratory activity, $m_h$ is an amplitude of a cardiac activity, $f_b$ is a frequency of the fundamental respiration signal, and $f_h$ is a frequency of the fundamental heartbeat signal;
   performing range Doppler processing of the mixed data by a computer to determine a range bin of interest in the plurality of range bins, wherein a portion of the mixed data acquired at the range bin of interest has a highest energy level of the mixed data;
   extracting data spectrum of the mixed data based on at least the portion of the mixed data acquired at the range bin of interest;
   applying adaptive filtering to the data spectrum by the computer to at least remove a spectrum peak of the fundamental respiration signal and a spectrum peak of the fundamental heartbeat signal mixed with one or more respiration harmonics from the data spectrum; and
   recovering the fundamental heartbeat signal based on a strongest heartbeat harmonic in the filtered data spectrum.

2. The method of claim 1 wherein:
   the range bins are scanned repeatedly by the small-scale radar to acquire multiple sets of the mixed data;
   the multiple sets of the mixed data are correspondingly summed together; and
   a phase noise correction is applied to the mixed data to reduce the phase noise due to sampling jitter before performing the range Doppler processing, wherein the phase noise correction is implemented by applying a phase shift to the mixed data at each range bin with respect to a mean phase in a reference range bin in a baseband.

3. The method of claim 1 wherein the small-scale radar is one of a group consisting of Ultra-Wideband (UWB) radar, frequency-modulated continuous wave (FMCW) radar, and impulse based radar.

4. The method of claim 1 wherein a scope of the plurality of range bins is between 0.2 meter and 3 meters, wherein the subject is located within the scope of the plurality of range bins.

5. The method of claim 1 further comprising performing clutter suppression to remove static background before performing the range Doppler processing of the mixed data.

6. The method of claim 5 wherein the clutter suppression is realized by high-pass filtering.

7. The method of claim 1 further comprising coherently combining the portion of the mixed data acquired at the range bin of interest with other portions of the mixed data acquired at nearby range bins to provide combined data before extracting the data spectrum, wherein the combined data has a greater signal to noise ratio (SNR) than the mixed data acquired at the range bin of interest.

8. The method of claim 7 wherein a distance between the range bin of interest and each of the nearby range bins is less than 0.2 meter.

9. The method of claim 7 wherein the portion of the mixed data acquired at the range bin of interest and the portion of the mixed data acquired at each nearby range bin are combined with different weights.

10. The method of claim 7 wherein coherently combining the portion of the mixed data acquired at the range bin of interest with the other portions of the mixed data acquired at nearby range bins is implemented by summing the portion of the mixed data acquired at the range bin of interest and the other portions of the mixed data acquired at nearby range bins together, correspondingly.

11. The method of claim 7 wherein extracting the data spectrum is based on the combined data.

12. The method of claim 1 further comprising performing spectrum analysis based on a spectrum model to find the spectrum peak of the fundamental respiration signal, and determine a lower limit of the adaptive filtering based on the spectrum peak of the fundamental respiration signal, wherein:

the spectrum model is $$Y(f, \tau_0) = A_T \sum_{k=-\infty}^{\infty} \sum_{l=-\infty}^{\infty} C_{k,l} \delta(f - kf_b - lf_h),$$

which is given by applying Fourier transform of $y(t, \tau) = A_T p(\tau - \tau_D(t)) e^{-j2\pi v_c \tau}$ at $\tau = \tau 0$, wherein $\tau 0 = d_0/c$, $C_{k,l}$ is an amplitude of intermodulation, and $\delta(f - kf_b - lf_h)$ provides impulse trains; and the lower limit of the adaptive filtering ensures the removal of the spectrum peak of the fundamental respiration signal and the spectrum peak of the fundamental heartbeat signal mixed with the one or more respiration harmonics.

13. The method of claim 12 wherein the adaptive filtering is implemented by a low-pass filter or a band-pass filter.

14. The method of claim 12 further comprising performing high-pass filtering to reduce DC residues before performing the spectrum analysis.

15. The method of claim 1 further comprising determining a harmonic order of the strongest heartbeat harmonic in the filtered data spectrum before recovering the fundamental heartbeat signal.

16. The method of claim 15 wherein the frequency of the fundamental heartbeat signal is recovered by dividing a frequency of the strongest heartbeat harmonic with the harmonic order of the strongest heartbeat harmonic.

* * * * *